United States Patent [19]

Fischer

[11] Patent Number: Plant 5,527

[45] Date of Patent: Aug. 6, 1985

[54] AFRICAN VIOLET PLANT NAMED SLEEPING BEAUTY

[75] Inventor: Arnold Fischer, Hanover, Fed. Rep. of Germany

[73] Assignee: Pan American Plant Company, Parrish, Fla.

[21] Appl. No.: 539,828

[22] Filed: Oct. 7, 1983

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of African violet plant named Sleeping Beauty particularly characterized by its large white, slightly ruffled flowers; compact rosette habit, with the flowers being carried on erect peduncles; floriferous habit, and its medium-light green foliage.

1 Drawing Figure

1

The present invention comprises a new and distinct cultivar of African violet plant, botanically known by *Saintpaulia ionantha,* and hereinafter referred to by the cultivar name Sleeping Beauty.

The new cultivar was referred to during the breeding and selection process by the designation V7-H27-W, and is a product of a planned breeding program. The basic objective of the breeding program was to create a new African violet cultivar having large white slightly ruffled blooms, medium-light green slightly ruffled foliage, and floriferous habit.

The new cultivar was originated from a cross made by Arnold Fischer in 1976 in a controlled breeding program in Hannover, Germany. The male and female parents are unknown at this time.

Sleeping Beauty was discovered and selected by Arnold Fischer as a flowering plant within the progeny of the stated cross in a controlled environment in Fallbrook, Calif. in 1977. Asexual reproduction of the new cultivar by leaf cuttings, as performed by me at West Chicago, Ill., and Parrish, Fla., has demonstrated that the combination of characteristics as herein disclosed for the new cultivar are firmly fixed and retained through successive generations of asexual reproduction.

Sleeping Beauty has not been observed under all possible environmental conditions. The phenotype may vary significantly with variations in environment such as temperature, light intensity and day length. The following observations, measurements and values describe the new cultivar as grown in Parrish, Fla. under greenhouse conditions which closely approximate those generally used in commercial practice.

The following traits have been repeatedly observed and are determined to be basic characteristics of Sleeping Beauty which in combination distinguish this African violet as a new and distinct cultvar:

(1) Large white flowers, which pink under certain growing conditions.

(2) Slightly ruffled flower petals.

(3) Compact rosette habit, with flowers borne on upright peduncles.

(4) Suitable for production in 10 cm. pots, flowering in 9 to 12 weeks depending upon growing conditions.

(5) Very floriferous, with flowers continuing to develop for weeks after onset of flowering.

(6) Medium-light green foliage, pubescent and with slightly ruffled crenate leaf margin.

2

The new cultivar is most similar to Abbey, a cultivar of applicant disclosed in U.S. Plant Pat. No. 4,115. Sleeping Beauty is principally distinguished from Abbey by its more vigorous and floriferous growth habit.

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under 5000 foot candles of natural light at approximately 10:30 A.M. in Parrish, Fla.

Botanical classification: *Saintpaulia ionantha,* Ramat. cv. Sleeping Beauty.

Parentage:

*Male parent.*—Unknown.

*Female parent.*—Unknown.

Propagation: The new cultivar holds its distinguishing characteristics through successive propagations by leaf cuttings.

Plant: From 4 cm. to 8 cm. tall when grown in pots, and approximately 20 cm. in diameter when fully grown. The growth rate is vigorous, and the general shape of the fully grown plant is round.

Leaves:

*Quantity.*—Abundant.

*Shape.*—Cordate with crenate margin.

*Diameter.*—50–75 mm.

*Texture.*—Pubescent, glossy.

*Ribs and veins.*—Pinnate.

*Color (upperside).*—137A.

*Color (underside).*—147D.

*Petioles.*—2–7 cm. In length.

Flowers:

*Buds.*—Size: Up to 1 cm.×1 cm. Shape: Round. Rate of opening: Normal. Color: Pale green 149D.

*Sepals.*—Shape: Lanceolate. Color: 139D.

*Phyllaries.*—Two, lanceolate. Color: 137C.

*Calyx.*—Shape: Funnel. Size: About 12 mm. diameter. Aspect: Hairy.

*Peduncle.*—Length: 30–70 mm. Character: Erect and rigid. Color: 143C.

*Individual flowers.*—Number of petals: Five. Size: 30–35 mm. diameter and 7 mm. deep. Shape: Cup when bloom first opens, becoming flat as flower matures. Color: Upperside: 155D and occasionally touched with 56B. Underside: 155D and occasionally touched with 56D. The white flower pinks occasionally, more noticably under cool growing conditions. Borne: Cymose clusters formed on upright peduncles, 3–7 cm. long. Flowering habit: Flowers profusely and intermittently year round, with blooms lasting 2–3 weeks after which petals dry up but do not drop. Finishes in 9–12 weeks when a 2¼″ plantlet is placed in a 10 cm. pot. Reproductive organs: Stamens: Borne singly on one side of of the ovary. Anthers: Basifixed, 2 mm. ×2 mm. yellow. Filaments: 2–3 mm., greenish-yellow. Pollen Color: Yellow. Pistels: Number: one. Style: one, 8–9 mm. long. Stigma: sticky, white. Ovaries: superior.

*Roots.*—Fiberous and fine.

*Disease resistance.*—No African violet diseases observed to date.

General observations: Sleeping Beauty has numerous flowers which are held aloft on erect peduncles above medium-green, slightly ruffled foliage. The single zygomorphic rotate flowers have five white petals which tend to pink occasionally, depending upon growing conditions. Sleeping Beauty may be finished in 9–12 weeks from a 2¼″ plantlet in a controlled environment.

I claim:

1. A new and distinct cultivar of African violet plant named Sleeping Beauty, as described and illustrated, and particularly characterized by its large white, slightly ruffled flowers; compact rosette habit, with the flowers being carried on erect peduncles; floriferous habit, and its medium-light green foliage.

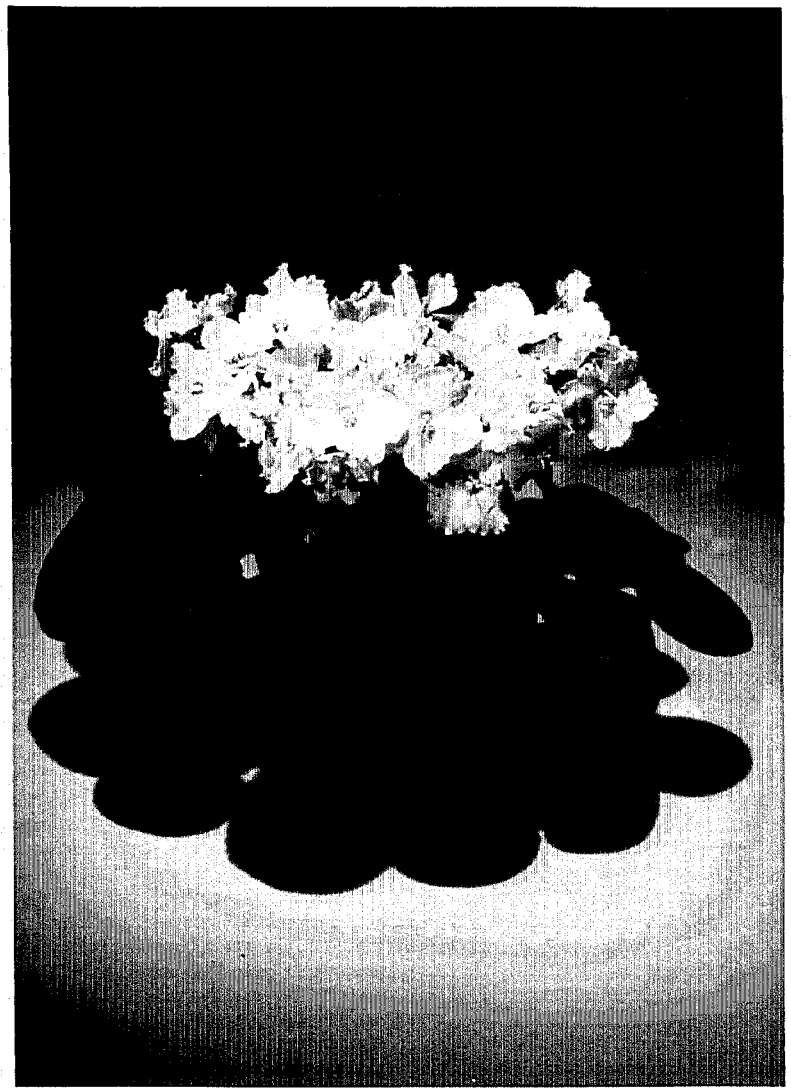

* * * * *